United States Patent [19]

Sugiyama et al.

[11] Patent Number: 4,551,272

[45] Date of Patent: Nov. 5, 1985

[54] DERIVATIVES OF DIPEPTIDE AND THEIR USE IN DETERMINING THE ACTIVITY OF CARBOXYPEPTIDASE A

[75] Inventors: Masami Sugiyama; Hiroko Shibuya; Yasushi Kasahara, all of Tokyo, Japan

[73] Assignee: Fujirebio Kabushiki Kaisha, Tokyo, Japan

[21] Appl. No.: 568,849

[22] Filed: Jan. 6, 1984

[51] Int. Cl.⁴ .......................................... C07C 103/52
[52] U.S. Cl. ............................................. 260/112.5 R
[58] Field of Search ................................. 260/112.5 R

[56] References Cited

PUBLICATIONS

Chem. Abstr. 146805s, vol. 101, 1984, Japan Abstr. 59, 66,897.
Chem. Abstr. vol. 101, (1984) 166272u, Jpn. JP 59, 85,299.
Chem. Abstr. vol. 80, (1974) 121330t.
Chem. Abstr., vol. 100, (1984) 7165z.
Chem. Abstr. vol. 85, (1976) 78364w.

*Primary Examiner*—Delbert R. Phillips
*Attorney, Agent, or Firm*—Flynn, Thiel, Boutell & Tanis

[57] ABSTRACT

Derivatives of dipeptide having the following general formula and their use as substrates for colorimetrically or spectrophotometrically measuring the activity of carboxypeptidase A:

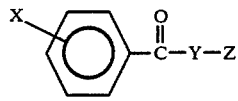

wherein X is OH in ortho or para position, or NH₂ or CH₃O in para position, Y is 6 Claims, 2 Drawing Figures

DERIVATIVES OF DIPEPTIDE AND THEIR USE IN DETERMINING THE ACTIVITY OF CARBOXYPEPTIDASE A

EXPLANATION OF THE INVENTION

This invention relates to derivatives of dipeptide having the following general formula and to their use as substrates for measuring the activity of carboxypeptidase A (hereinafter referred to as CP-A for short).

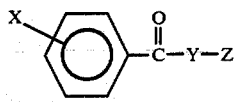

wherein X is OH in ortho or para position, or $NH_2$ or $CH_3O$ in para position, Y is

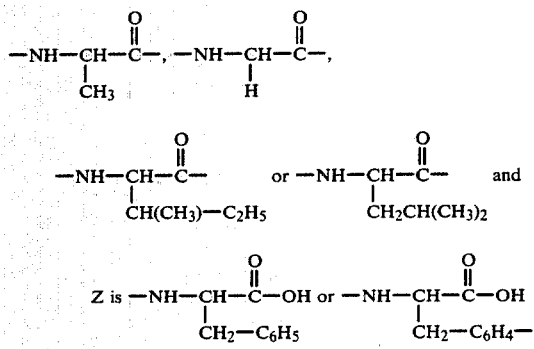

Z is

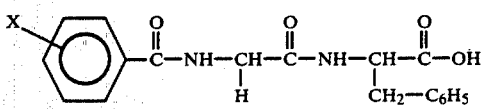

excluding derivatives of dipeptide having the following general formula:

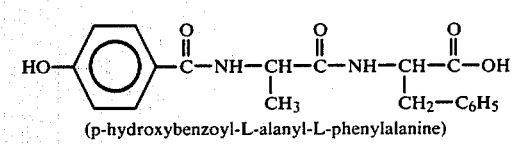

wherein X is OH or $CH_3O$.

CP-A is a protein-decomposing enzyme which is found in the pancreas and the blood serum. The activity of CP-A depends on the disease which is present and its extent. Accordingly, by measuring the activity of the CP-A, the extent to which a disease has spread can be measured.

According to an aspect of this invention, there is provided derivatives of dipeptide having the following formulas:

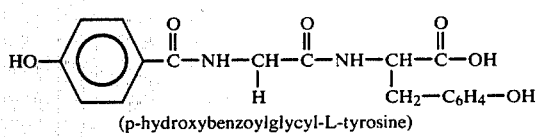

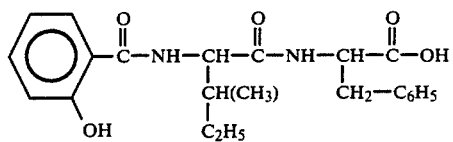

(o-hydroxybenzoyl-L-isoleucyl-L-phenylalanine)

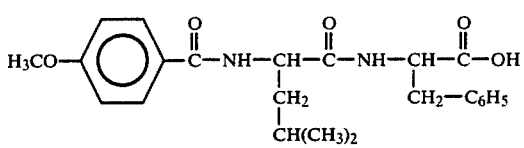

(p-methoxybenzoyl-L-leucyl-L-phenylalanine)

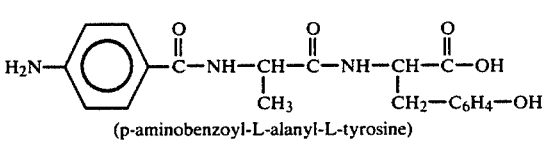

(p-aminobenzoyl-L-alanyl-L-tyrosine)

According to a second aspect of this invention, there is provided methods for measuring colorimetrically or spectrophotometrically the activity of CP-A by using dipeptide derivatives of this invention as substrate. In the following, "Ala", "Phe", "Gly" and "Tyr" are the abbreviations of "alanyl or alanine", "phenylalanyl or phenylalanine", "glycyl or glycine" and "tyrosyl or tyrosine", respectively, and further "NADH" means "reduced nicotinamide adenine dinucleotide" and "NADPH" means "reduced nicotinamide adenine dinucleotide phosphate".

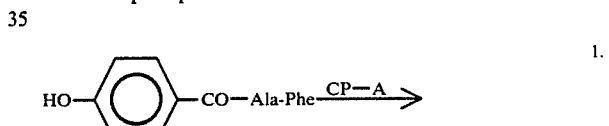
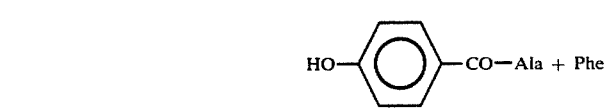
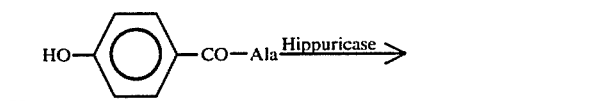
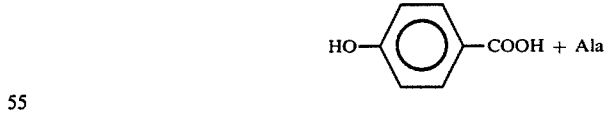
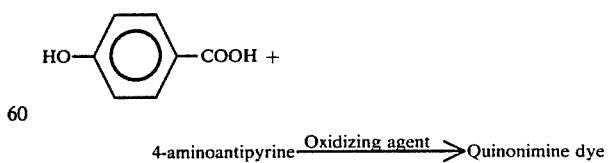

The concentration of the quinonimine dye produced is colorimetrically measured, and the activity of CP-A is calculated. Preferred embodiments of the colorimetrical method will be illustrated in the following Examples 1 and 2.

2.

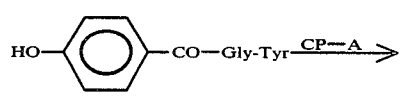

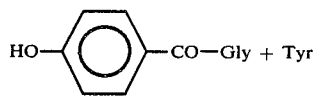

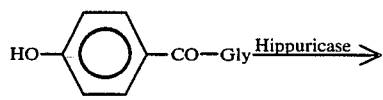

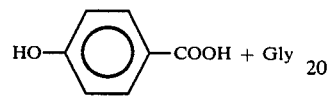

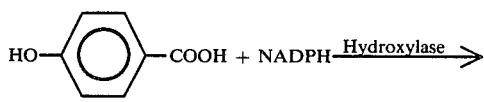

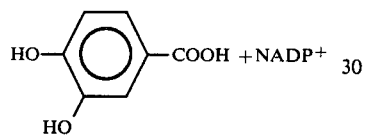

The decrease of the absorbance by NADPH is spectrophotometrically measured at 340 nm of light during the course of the reaction by using a reaction rate analyzer, and the activity of CP-A is calculated. Preferred embodiments will be illustrated in the following Examples 3 and 4. In Example 5, NADH is used instead of NADPH.

3.

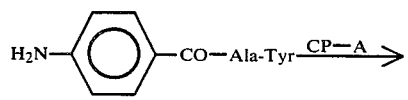

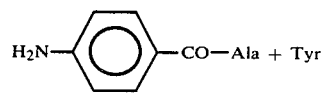

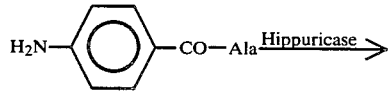

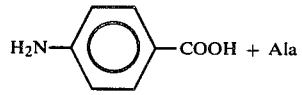

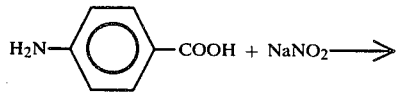

-continued

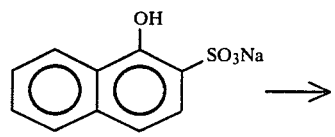

(Coupling reagent)

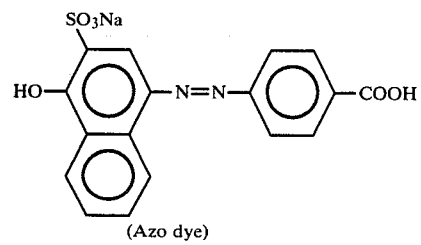

(Azo dye)

The concentration of the azo dye produced is colorimetrically measured, and the activity of CP-A is calculated. Preferred embodiment of this colorimetrical method will be illustrated in the following Example 6.

Dipeptide derivatives of the present invention are synthesized as follows:

1. Synthesis of p-hydroxybenzoyl-L-alanyl-L-phenylalanine: 0.1 g (0.1 mol) of triethylamine was added to a suspension of 23.0 g (0.1 mol) of L-phenylalanine ethyl ester·HCl in 500 ml of dichloromethane, and to this mixture in an ice bath was added 22.3 g (0.1 mol) of carbobenzoxy-L-alanine, and then 19.2 g (0.1 mol) of 1-ethyl-3(3-dimethyaminopropyl) carbodiimide·HCl was added to the mixture. This mixture was stirred for three hours. This reaction mixture was washed with a 0.1% aqueous solution of Na₂CO₃ three times and with a 0.1 N HCl solution three times, and then with distilled water three times. Thereafter, the mixture was dried over anhydrous sodium sulfate, and dichloromethane was removed from the mixture under reduced pressure to obtain carbobenzoxy-L-alanyl-L-phenylalanine ethyl ester. This ester was dissolved in 260 ml of 25% HBr in glacial acetic acid, and this solution was stirred for one hour. To this solution was added 5 l of absolute ethyl ether to produce a precipitate. The precipitate was filtered and washed with ethyl ether to obtain L-alanyl-L-phenylalanine ethyl ester·HBr.

17.3 g (0.05 mol) of L-alanyl-L-phenylalanine ethyl ester·HBr was suspended in 250 ml of dichloromethane, and to this susension were added 5.1 g (0.05 mol) of triethylamine and 9 g (0.05 mol) of p-acetoxybenzoic acid, and then 9.6 g (0.05 mol) of 1-ethyl-3(3-dimethylaminopropyl)carbodiimide·HCl was added in an ice bath. This mixture was stirred for three hours, and then was washed with a 0.1% aqueous solution of Na₂CO₃ and with a 0.1 N HCl solution three times and then with distilled water three times, and was dried over anhydrous sodium sulfate. Dichloromethane was removed from the dried mixture under reduced pressure to obtain p-acetoxybenzoyl-L-alanyl-L-phenylalanine ethyl ester.

Figure 1:
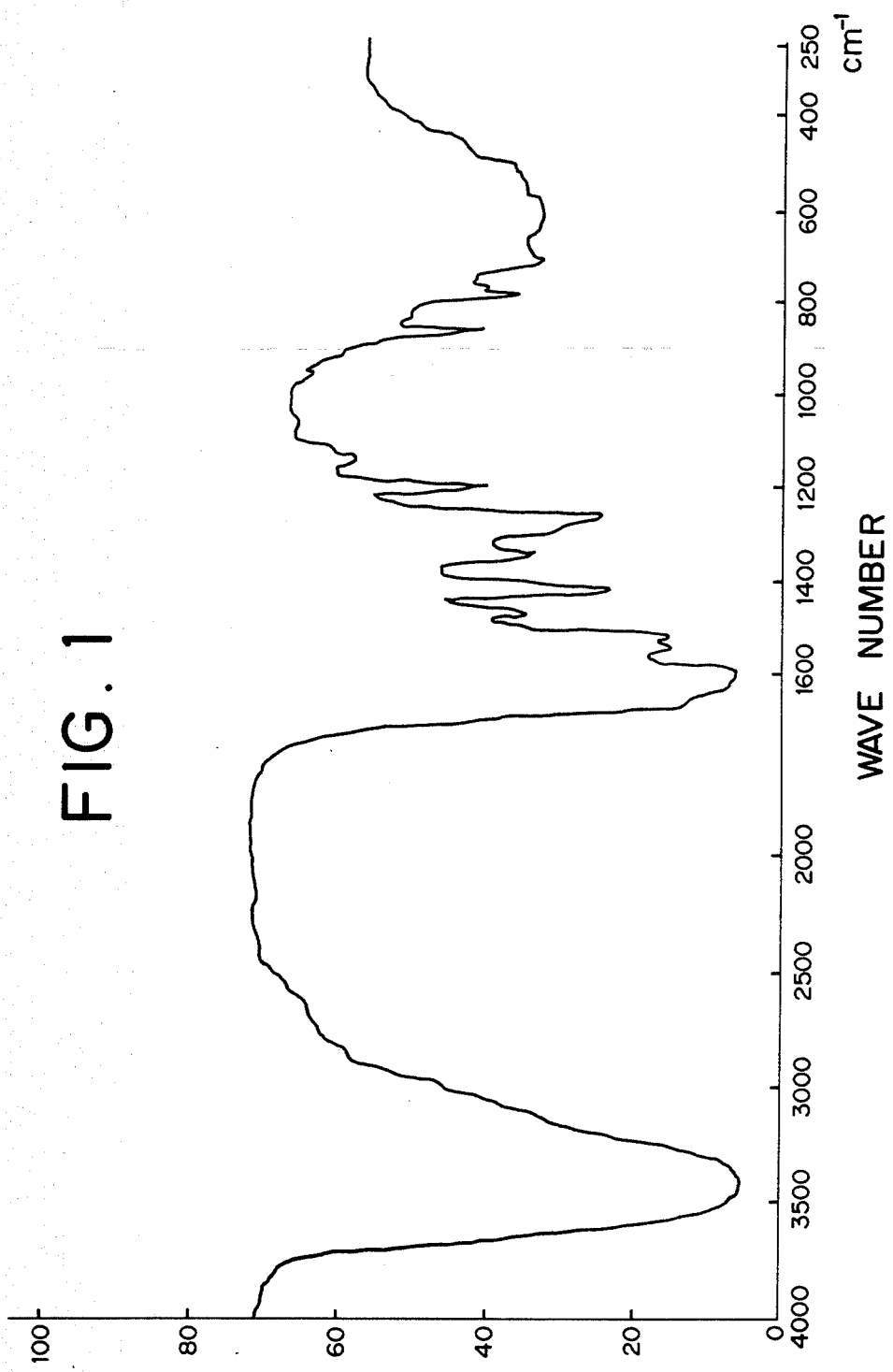
FIG. 1 is the IR spectrum of p-hydroxybenzoyl-L-alanyl-L-phenylalanine.

8.5 g (0.02 mol) of ester obtained above was dissolved in 50 ml of methanol, and to this solution was added 70 ml of a 1 N NaOH aqueous solution in an ice bath, and the solution was stirred for two hours at room temperature. After the pH of the solution was adjusted to 7.0 with a 1 N HCl solution, the solvent was distilled off from the solution under reduced pressure to obtain a residue, and this residue was purified by absorption chromatography to obtain p-hydroxybenzoyl-L-alanyl-L-phenylalanine in an amount of 6.4 g. m.p. 211° C.-211.6° C. (decomposed). Its infrared absorption spectrum is shown in FIG. 1.

2. Synthesis of p-hydroxybenzoylglycyl-L-tyrosine: 21 g (0.1 mol) of carbobenzoxyglycine was dissolved in 500 ml of dichloromethane, and to this solution was added 24.5 g (0.01 mol) of L-tyrosine ethyl ester, and after 19.2 g (0.1 mol) of 1-ethyl-3(3-dimethylaminopropyl)carbodiimide·HCl was added in an ice bath, the solution was stirred overnight.

The reaction mixture was washed with a 0.1% aqueous solution of Na₂CO₃ three times and with distilled water three times, and then dried over anhydrous sodium sulfate. Dichloromethane was removed from the reaction mixture under reduced pressure to obtain carbobenzoxyglycyl-L-tyrosine ethyl ester.

250 ml of 25% HBr in glacial acetic acid was added to carbobenzoxyglycyl-L-tyrosine ethyl ester obtained above, and after the mixture was stirred for 30 minutes at room temperature, 5 l of absolute ethyl ether was added to the mixture to produce a precipitate. The precipitate was washed with ethyl ether to obtain glycyl-L-tyrosine ethyl ester·HBr.

17.4 g (0.05 mol) of glycyl-L-tyrosine ethyl ester·HBr, 9 g (0.05 mol) of p-acetoxybenzoic acid and 5.1 g (0.05 mol) of triethylamine were dissolved in 250 ml of dichloromethane, and after the solution was cooled to 0° C., 9.6 g (0.05 mol) of 1-ethyl-3(3-dimethylaminopropyl)carbodiimide·HCl was added to the solution, and the solution was stirred overnight. The reaction mixture was washed with a 0.1% aqueous solution of Na₂CO₃ and with a 0.1 N HCl solution, and was dried over anhydrous sodium sulfate. Dichloromethane was removed from the mixture under reduced pressure to obtain p-acetoxybenzoylglycyl-L-tyrosine ethyl ester.

Figure 2:
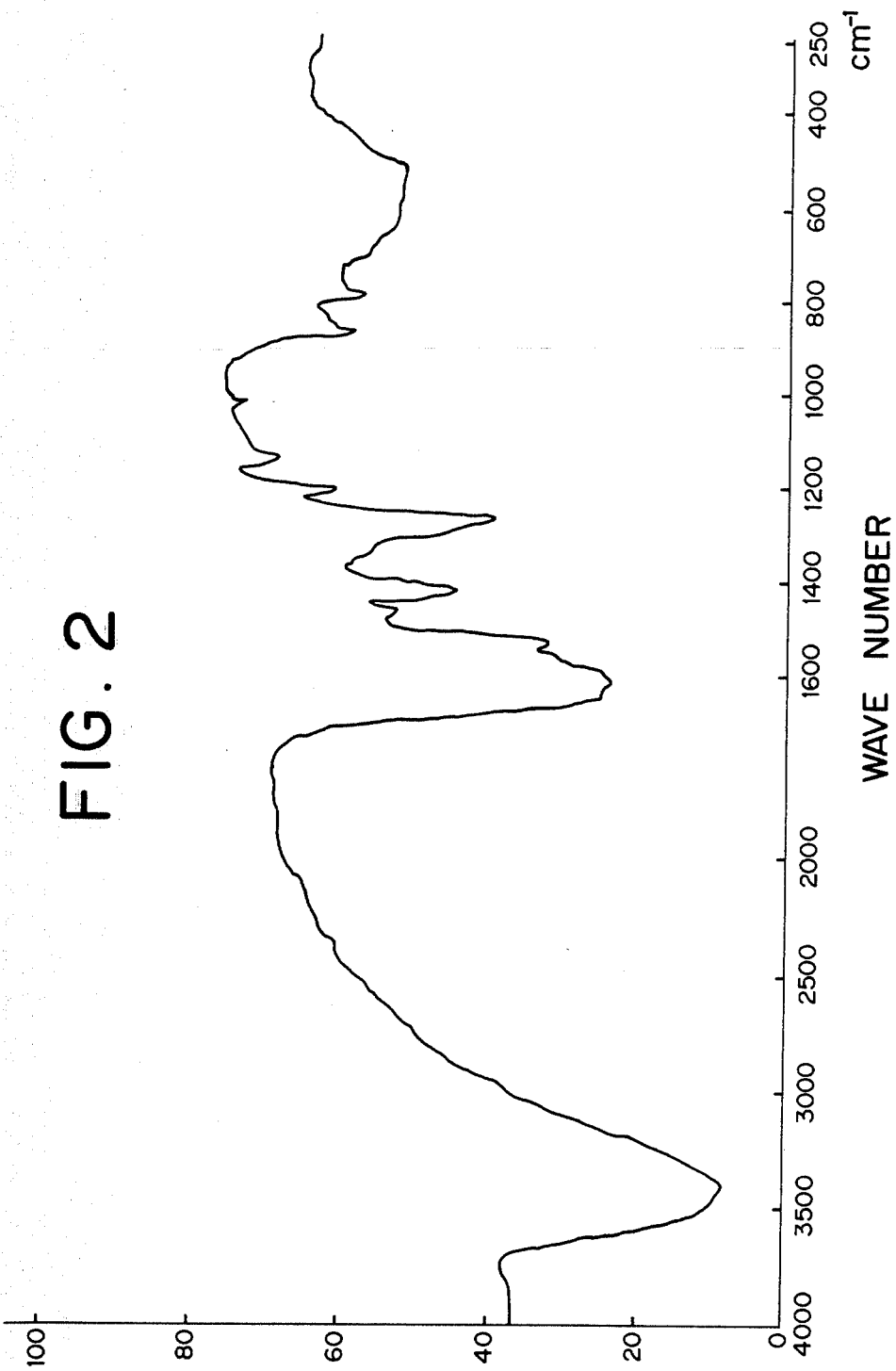
FIG. 2 is the IR spectrum of p-hydroxybenzoylglycyl-L-tyrosine.

8.6 g (0.02 mol) of p-acetoxybenzoylglycyl-L-tyrosine ethyl ester obtained above was dissolved in 50 ml of methanol, and to this solution was added 70 ml of a 1 N NaOH aqueous solution, and the solution was stirred for one hour at room temperature. The pH of the solution was adjusted to 7.0 with a 1 N HCl solution, and the solvent was distilled off from the solution under reduced pressure. The residue was dissolved in methanol, and the insoluble matter was filtered off. To the filtrate was added ethyl ether to produce a precipitate. This precipitate was filtered off to obtain p-hydroxybenzoylglycyl-L-tyrosine in an amount of 5 g. m.p. 184° C.-210° C. (decomposed). Its infrared absorption spectrum is shown in FIG. 2.

3. Synthesis of o-hydroxybenzoyl-L-isoleucyl-L-phenylalanine: 4.6 g of o-hydroxybenzoyl-L-isoleucyl-L-phenylalanine was obtained by repeating the procedure as shown above (2. Synthesis of p-hydroxybenzoylglycyl-L-tyrosine) except that 26.5 g of carbobenzoxyisoleucine was used instead of 21 g of carbobenzoxyglycine, 20 g of L-phenylalanine ethyl ester·HCl was used instead of 24.5 g of L-tyrosine ethyl ester·HCl, and 9 g of o-acetoxybenzoic acid was used instead of 9 g of p-acetoxybenzoic acid.

4. Synthesis of p-methoxybenzoyl-L-leucyl-L-phenylalanine: 3.6 g of p-methoxybenzoyl-L-leucyl-L-phenylalanine was obtained by repeating the procedure as shown above 2 except that 26.5 g of carbobenzoxy-L-leucine was used instead of 21 g of carbobenzoxyglycine and 7.6 g of p-methoxybenzoic acid was used instead of 9 g of p-acetoxybenzoic acid.

5. Synthesis of p-aminobenzoyl-L-alanyl-L-tyroine: 4.4 g of p-aminobenzoyl-L-alanyl-L-tyrosine was obtained by repeating the procedure as shown above 2 except that 22.3 g of carbobenzoxy-L-alanine was used instead of 21 g of carbobenzoxyglycine and 8.9 g of p-acetamidobenzoic acid was used instead of 9 g of p-acetoxybenzoic acid.

The activity of carboxypeptidase A was determined as follows:

EXAMPLE 1

0.1 ml of serum containing carboxypeptidase A was added to 0.5 ml of a test reagent solution (pH 7.8) containing 10 mM p-hydroxybenzoyl-L-alanyl-L-phenylalanine, 0.1 M sodium chloride, 3000 U/l hippuricase, 2.5 mM 4-aminoantipyrine and 100 mM N-2-hydroxyethyl piperazine-N-2-ethane sulfonic acid (hereinafter referred to as HEPES for short). The mixture was incubated at 37° C. for 20 minutes. To this reaction mixture was added 1.5 ml of a reaction termination solution containing 6.5 mM sodium periodate. The mixture was incubated at 37° C. for five minutes, so that quinonimine dye was formed. The absorbance of the reaction mixture was measured at a light wavelength of 505 nm. This absorbance is referred to as Absorbance A.

Separately, for a blank (comparison) test, in the procedure as mentioned above, 1.5 ml of a reaction termination solution containing 6.5 mM sodium periodide was added to the test reagent solution before 0.1 ml of serum containing carboxypeptidase A was added to the test reagent solution, and in the same manner as described above, the absorbance of the blank test reagent was measured at a light wavelength of 505 nm. This absorbance is referred to as Absorbance B.

The activity value (mU/ml) of carboxypeptidase A can be calculated by the following equation:

$$mU/ml = \frac{A - B}{\text{Molecular extinction coefficient } (\epsilon)} \times \frac{1}{\text{Reaction time (5 min.)}} \times \frac{1}{\text{Light path length (cm)}} \times \frac{2.1}{0.1} \times 10^6$$

where
  $\epsilon = 12000$ (Molecular extinction coefficient of quinonimine dye)

By repeating the above-described test 20 times, using the same samples, the following results were obtained:
  Activity value (mU/ml) = 5.1 (nmol/ml/min)
  Coefficient of variation (CV) = 3.4%

EXAMPLE 2

The activity of CP-A was determined by repeating the procedure as shown in Example 1 except that p-hydroxybenzoylglycyl-L-tyrosine or o-hydroxybenzoyl-L-isoleucyl-L-phenylalanine was used instead of p-hydroxybenzoyl-L-alanyl-L-phenylalanine.

The following results were obtained:

Activity value (*mU*/ml) = 2.4 (*n*mol/ml/min)
Activity value (*mU*/ml) = 1.2 (*n*mol/ml/min)
Coefficient of variation (*CV*) = 4.5%
Coefficient of variation (*CV*) = 6.0%

EXAMPLE 3

0.05 ml of serum (same as used in Example 1) was added to 0.5 ml of a test reagent solution (pH 8.0) containing 10 mM p-hydroxybenzoylglycyl-L-tyrosine, 3000 U/l hippuricase, 0.2 mM NADPH, 10000 U/l p-hydroxybenzoate hydroxylase and 100 mM boric acid.

The decrease of the absorbance by the solution was measured at 340 nm of light at a temperature of 37° C. during the course of the reaction. For the measurement, a reaction rate analyzer was used, in which the reaction time was five minutes. The activity value (mU/ml) of CP-A was automatically printed out in the analyzer.

The calculation of activity was performed according to the following formula:

$$mU/ml = \frac{\text{Decrease in absorbance at 340 nm}}{\text{Reaction time (5 min)}} \times$$

$$\frac{1}{\text{Molecular extinction coefficient } (\epsilon)} \times \frac{1}{\text{Light-path length (cm)}} \times$$

$$\frac{0.55}{0.05} \times 10^6$$

wherein $\epsilon = 6.22 \times 10^3$ (Molecular extinction coefficient of NADPH)

The results of the measurements, repeated 20 times, were as follows:

Activity value (mU/ml)=6.2 (nmol/ml/min)
Coefficient of variation (CV)=5.2%

EXAMPLE 4

The activity of CP-A was determined by repeating the procedure as shown in Example 3 except that o-hydroxybenzoyl-L-isoleucyl-L-phenylalanine was used instead of p-hydroxybenzoylglycyl-L-tyrosine, salicylate hydroxylase was used instead of p-hydroxybenzoate hydroxylase, and nicotinamide adenine dinucleotide in reduced form (NADH) was used instead of NADPH.

The following results were obtained:
Activity value (mU/ml)=1.1 (nmol/ml/min)
Coefficient of variation (CV)=7.0%

EXAMPLE 5

The activity of CP-A was determined by repeating the procedure as shown in Example 3 with a mixture prepared by adding 0.05 ml of serum (same as used in Example 1) to 0.5 ml of a test reagent solution (pH 8.0) containing 30 mM p-methoxybenzoyl-L-leucyl-L-phenylalanine, 1000 U/l hippuricase, 0.2 mM NADH, 20000 U/l p-methoxybenzoate hydroxylase and 100 mM phosphoric acid.

The following results were obtained:
Activity value (mU/ml)=2.5 (nmol/ml/min)
Coefficient of variation (CV)=4.7%

EXAMPLE 6

0.05 ml of serum (same as used in Example 1) containing CP-A was added to 0.5 ml of a test reagent solution (pH 8.0) containing 20 mM p-aminobenzoyl-L-alanyl-L-tyrosine, 0.5 M NaCl, 3000 U/l hippuricase and 100 mM boric acid. After this mixture was allowed to stand at 37° C. for 20 minutes, 0.5 ml of a solution containing 2 mM NaNO₂ and 1 mM NaOH was added to the mixture, and the mixture was allowed to stand at room temperature for 10 minutes. To the mixture was added 0.5 ml of a reagent solution containing 1 mM potassium 1-naphthol-2-sulfonate, 50 mM boric acid and 200 mM NaOH. The absorbance by the solution was measured at 505 nm of light. This absorbance is referred to as Absorbance A.

Absorbance B was measured by repeating the procedure as shown above except that 0.05 ml of an aqueous solution containing 10 μM p-aminobenzoic acid was used instead of 0.05 ml of serum, and Absorbance C was measured by repeating the procedure as shown above except that 0.05 ml of distilled water was used instead of 0.05 ml of serum.

The activity value (mU/ml) of CP-A can be calculated by the following equation:

$$mU/ml = \frac{A - C}{B - C} \times 10$$

By repeating the above-described test 20 times, the following results were obtained:
Activity value (mU/ml)=1.7 (nmol/ml/min)
Coefficient of variation (CV)=5.3%

We claim:

1. A dipeptide derivative having the general formula:

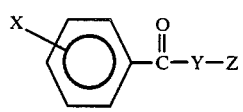

wherein X is OH in ortho or para position, or NH₂ or CH₃O in para position, Y is

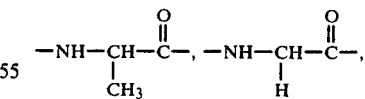

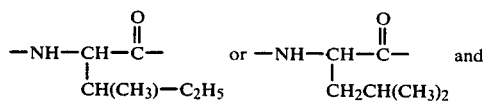

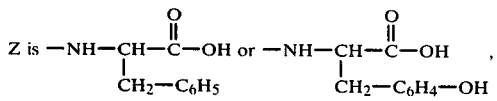

excluding however dipeptide derivatives having the general formula:

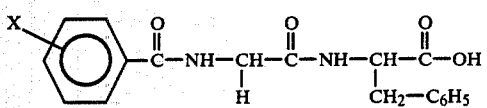

wherein X is OH or CH₃O.

2. A dipeptide derivative as claimed in claim 1, wherein said derivative is p-hydroxybenzoyl-L-alanyl-L-phenylalanine.

3. A dipeptide derivative as claimed in claim 1, wherein said derivative is p-hydroxybenzoylglycyl-L-tyrosine.

4. A dipeptide derivative as claimed in claim 1, wherein said derivative is o-hydroxybenzoyl-L-isoleucyl-L-phenylalanine.

5. A dipeptide derivative as claimed in claim 1, wherein said derivative is p-methoxybenzoyl-L-leucyl-L-phenylalanine.

6. A dipeptide derivative as claimed in claim 1, wherein said derivative is p-aminobenzoyl-L-alanyl-L-tyrosine.

* * * * *